United States Patent [19]

Stueve

[11] Patent Number: 6,076,966
[45] Date of Patent: Jun. 20, 2000

[54] STAND FOR X-RAY IMAGE QUALITY TESTING

[75] Inventor: Richard Stueve, Shawnee, Kans.

[73] Assignee: GE Marquette Medical Systems, Inc., Milwaukee, Wis.

[21] Appl. No.: 09/072,882

[22] Filed: May 5, 1998

[51] Int. Cl.[7] ...................................................... A61B 6/08
[52] U.S. Cl. .......................................... 378/207; 378/205
[58] Field of Search .................................... 378/207, 205, 378/206, 162, 19, 208

[56] References Cited

U.S. PATENT DOCUMENTS

| | | | |
|---|---|---|---|
| 4,048,507 | 9/1977 | de Gaston | 378/205 X |
| 4,123,660 | 10/1978 | Horwitz | 378/206 X |
| 4,551,678 | 11/1985 | Morgan et al. | 324/300 |
| 4,578,806 | 3/1986 | Grass et al. | 378/205 X |
| 5,212,720 | 5/1993 | Landi et al. | 378/206 |

FOREIGN PATENT DOCUMENTS 632454  1/1928  France ................................. 378/206

OTHER PUBLICATIONS

Photograph of prior art test stand prior to 1980.

*Primary Examiner*—David P. Porta
*Attorney, Agent, or Firm*—Michael Best & Friedrich; Christine G. Cabou; Phyllis Y. Price

[57] ABSTRACT

A test stand for use in testing the performance of an X-ray system constructed and arranged to project an X-ray beam along a defined path. The stand includes a vertical base, a first support extending horizontally from one end of the base for positioning a first test object at a first location relative to the path and a second support extending horizontally from the other end of the base for positioning a second test object at a second position relative to said path and spaced from said first test object. Each support includes a test object receiver and one of the receivers is adjustable in a direction perpendicular to the path. A leveler is mounted on the stand for leveling the first and second supports relative to the horizontal. Each of the supports is pivotally mounted on the base and holding members are coupled to the base and the supports for holding each of said supports in a horizontal orientation, the holding members being releasable to permit the supports to be pivoted toward the frame for storage.

13 Claims, 5 Drawing Sheets

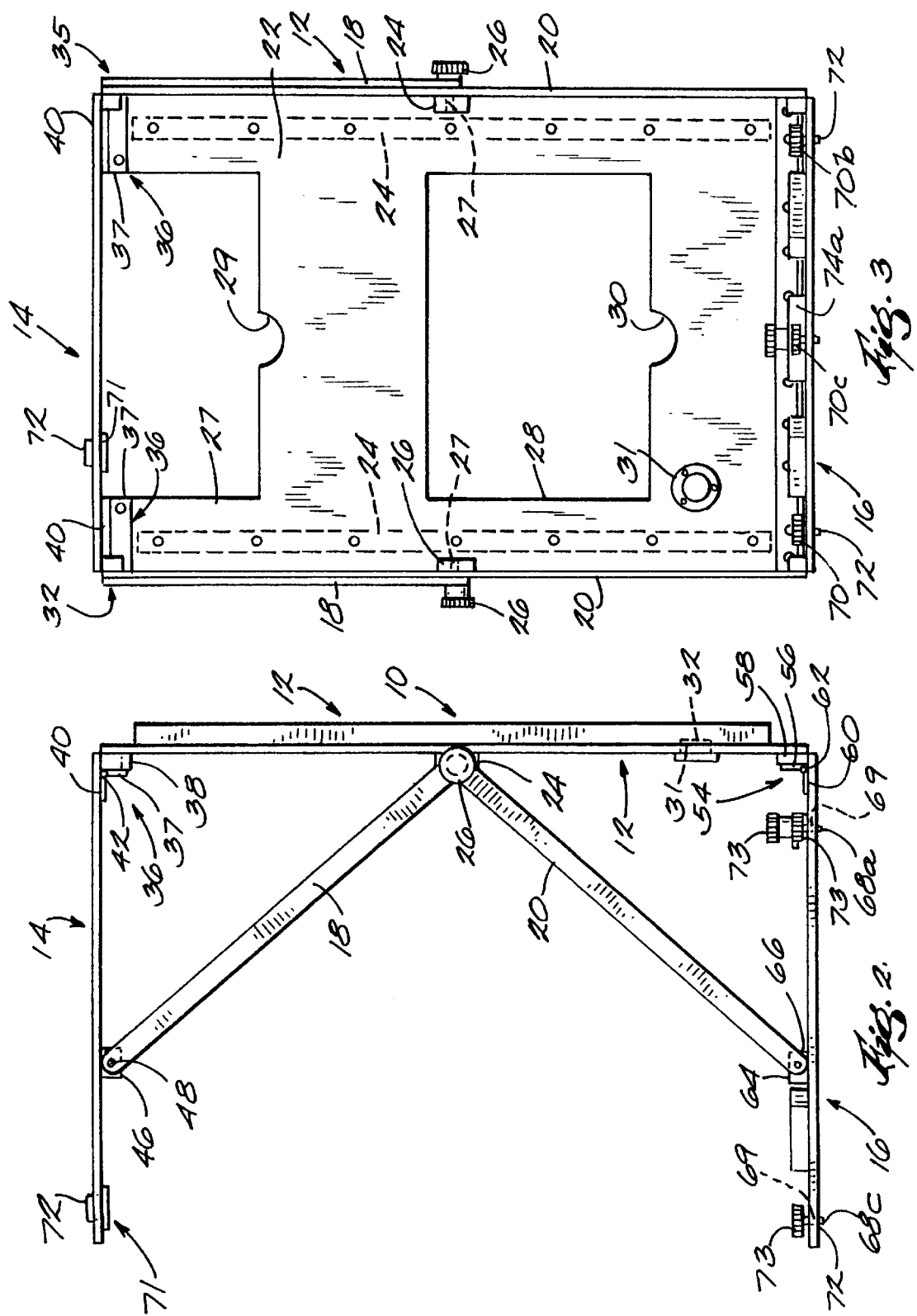

STAND FOR X-RAY IMAGE QUALITY TESTING

BACKGROUND OF THE INVENTION

This invention relates to test stands and more particularly to tests stands for X-ray image quality testing.

Various tests have been performed for evaluating the image quality performance of X-ray systems such as those used in cardiac catherization laboratories. For this purpose, of various test objects such as attenuators and phantoms are positioned in the path of the X-ray beam to indicate various characteristics of the equipment, such as, collimator congruence and accuracy, fluoroscopy, cine, and/or digital exposure rates, video resolution, field of view size accuracy, image on frame optical density, monitor brightness and contrast, image spatial resolution, intensifier percent contrast, image contrast resolution. However, in previous X-ray tests there has been no uniformity in the placement or arrangement of test phantoms and attenuators so that the test results attained from different machines could not necessarily be correlated or compared.

SUMMARY OF THE INVENTION

It is an object of the invention to provide a new and improved test stand for measuring the performance of X-ray systems.

Another object of the invention is to provide a test stand for measuring the performance of X-ray systems which provides uniform results for a variety of systems.

A further object of the invention is to provide a test stand for X-ray systems which ensures uniformity of test results.

Yet another object of the invention is to provide a test stand for measuring X-ray system performance which accurately positions the test objects relative to the X-ray equipment.

It is a further object of the invention to provide a test stand for measuring the performance of X-ray equipment which is convenient and easy to use.

These and other objects and advantages of the present invention will become more apparent from the detailed description thereof taken with the accompanying drawings.

In general terms, the invention comprises a stand for use in testing the performance of an X-ray system constructed and arranged to project an X-ray beam along a defined path. The stand includes a first support for positioning a first test object at a first location relative to the path, a second support for positioning a second test object at a second position relative to the path and spaced from the first object and a receiver on at least one of the supports for receiving a test object. According to a more specific aspect of the invention, the first and second supports are spaced apart vertically, and a leveler is provided for leveling the first and second supports relative to the horizontal. According to another more specific aspect of the invention, the test stand includes a base, each of the supports being mounted on the base in a vertically spaced apart relation, and at least one of the receivers is adjustable horizontally. According to yet another more specific aspect of the invention, the stand includes a generally vertically extending base, each of the supports being pivotally mounted in spaced apart relation on the base, and holding members are provided for holding each of the supports in a horizontal orientation. The holding members are releasable to permit the supports to be pivoted toward the frame for storage. According to yet another more specific aspect of the invention, each receiver has a predetermined shape for receiving test objects having a complimentary shape and for fixing the test objects in a predetermined orientation when positioned in the receivers.

BRIEF DESCRIPTION OF THE DRAWINGS

FIG. 2 is a side elevational view of the test stand illustrated in FIG. 1;

FIG. 3 is a front view thereof;

FIGS. 6, 7 and 8 show examples of test objects used with the test stand of FIGS. 2–4.

DETAILED DESCRIPTION OF THE PREFERRED EMBODIMENT

Figure 1:
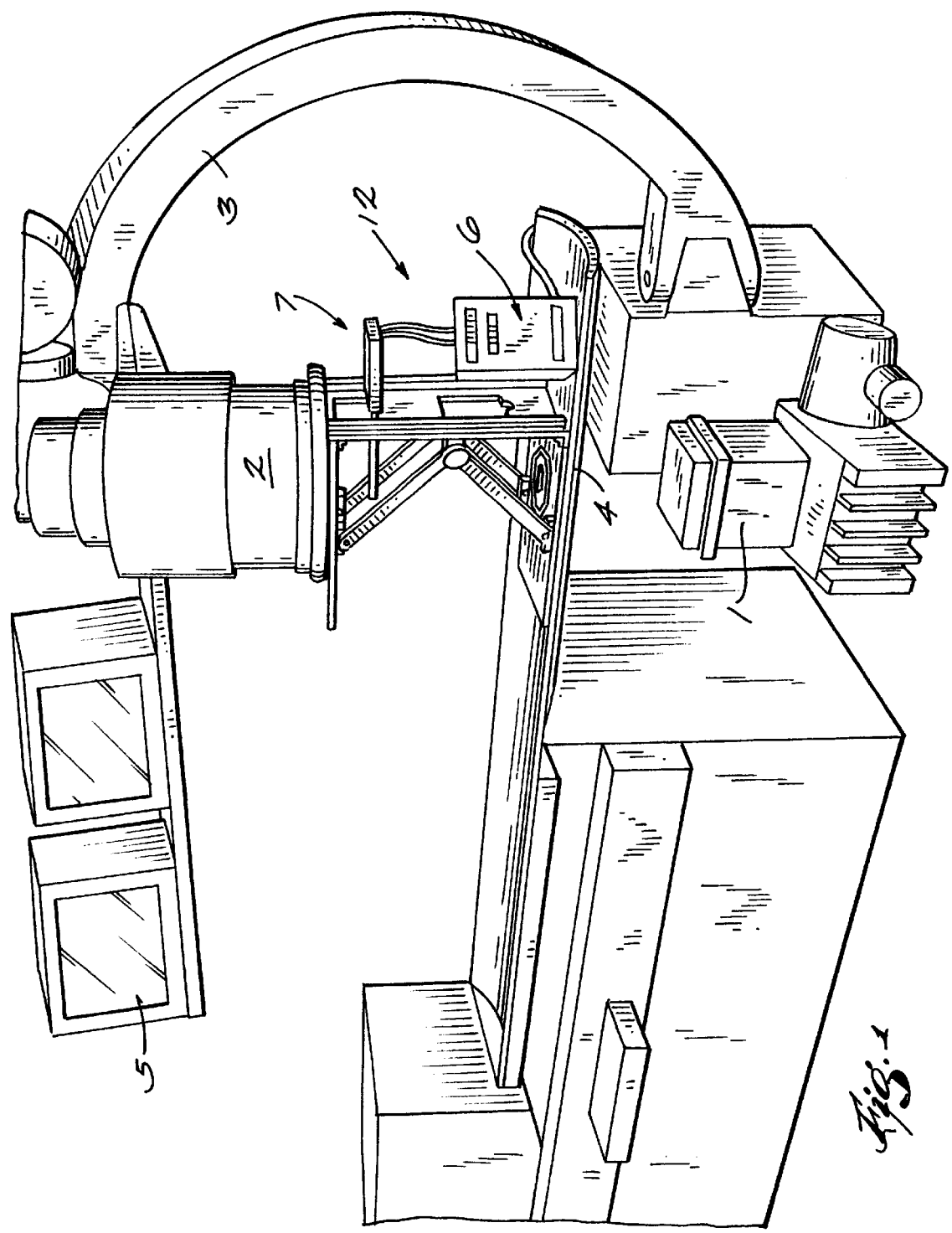
FIG. 1 is a perspective view showing the manner in which the test stand according to the invention is positioned relative to an X-ray apparatus when in use.

A conventional X-ray apparatus is shown in FIG. 1 to include an X-ray tube assembly 1, an image intensifier assembly 2 mounted on a rotating gantry 3, and a patient table 4. As those skilled in the art will appreciate, the X-ray tube assembly 1 projects an X-ray beam upwardly to the image intensifier assembly which enhances the image for display on a monitor 5 or for being stored in memory or for printing. The test procedure may also includes the use of a dosimeter 6 having a probe 7 adapted to be positioned between the X-ray tube assembly 1 and the image intensifier 2 for measuring the radiation level. The test stand 10 according to the invention is constructed and arranged to be positioned on the patient table 4 during the testing procedure to be described below.

Figure 4:
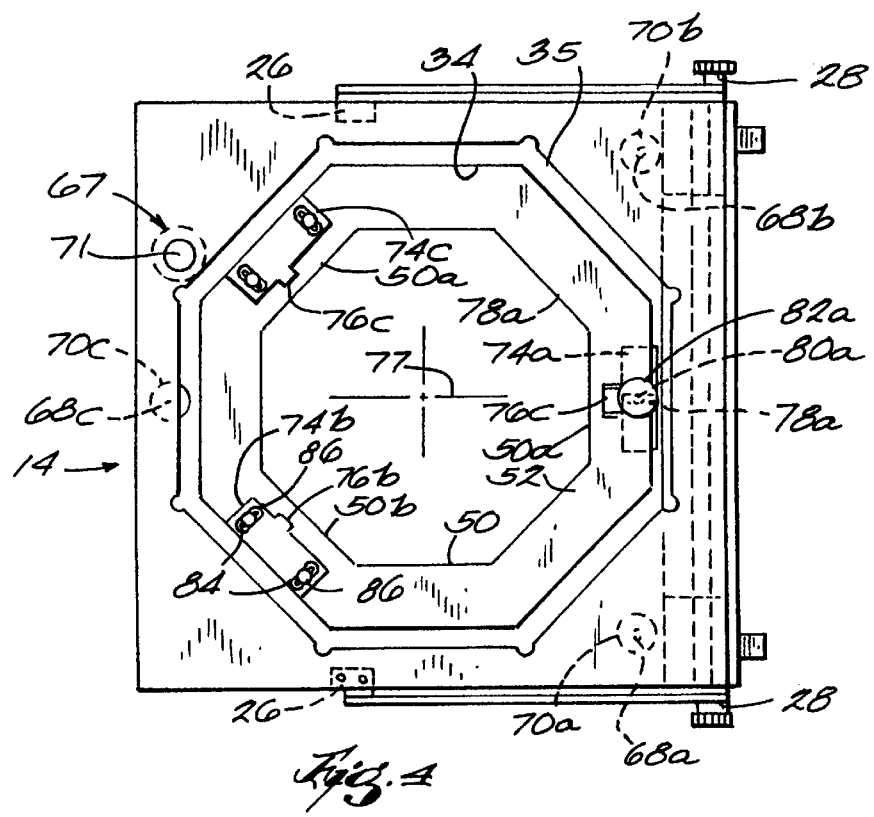
FIG. 4 is a top view thereof.
Figure 6:
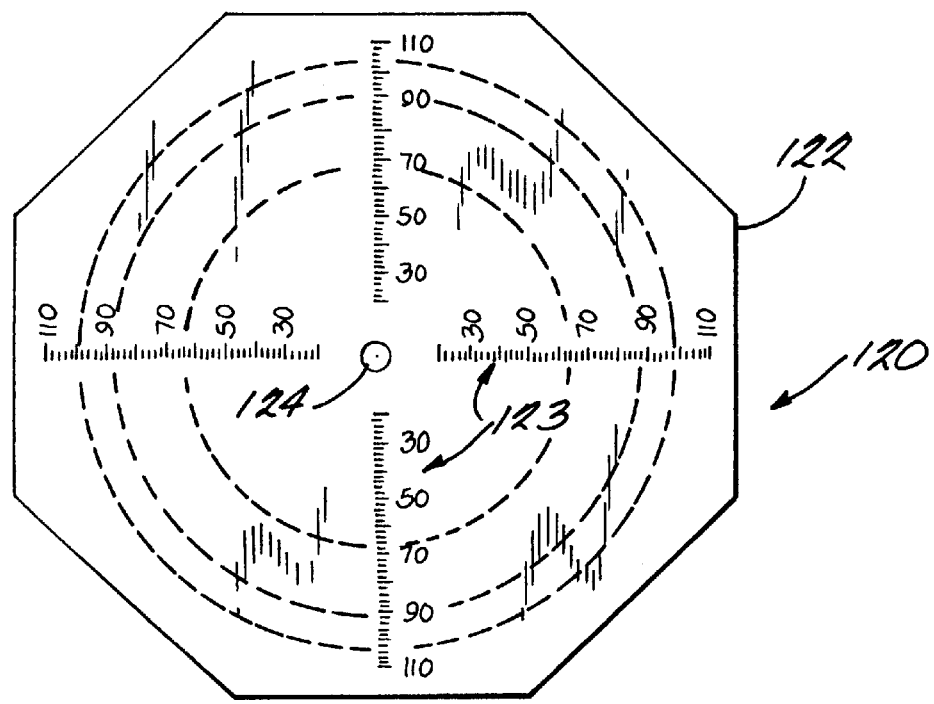

The X-ray image quality test system includes the test stand 10 according to the preferred embodiment of the invention shown in FIGS. 2–4 and a plurality of test objects, examples of which are shown in FIGS. 6 and 7. The test stand 10 and the test objects, such as phantoms and attenuators are employed for testing the performance of an X-ray or fluoroscopic system as shown in FIG. 1. The test stand 10 is shown in FIGS. 2–4 to include a vertical back panel 12 and upper and lower support panels 14 and 16 which are respectively hinged to the upper and lower edges of the back panel 12. Pairs of upper and lower releasable support arms 18 and 20 hold the upper and lower support panels 14 and 16 in their operative positions perpendicular relative to the back panel 12 when the arms 18 and 20 are secured as shown in FIG. 2, and which permit the panels 14 and 16 to be folded inwardly toward the back panel 12 for storage when the arms 18 and 20 are released.

The back panel 12 comprises a flat, rectangular plate having an elongate support bar 23 fixed along each lateral edge of its rear surface. In addition, a support block 24 is fixed at about the mid point of each edge of the forward side of panel 12. A threaded bore 25 is formed laterally through each support block 24 for receiving a thumb screw 28 each of which releasably engages a hole formed in one end of one of the support arms 18 and 20 on its respective side of the assembly. A pair of rectangular openings 27 and 28 may be formed in the panel 12 to facilitate access to the space between the upper and lower panels 14 and 16 and for use when the base is used to support test objects in a horizontal position. Semi-circular slots 29 and 30 are formed in the lower edges of openings 27 and 28, respectively, for receiving radiation probes, such as probe 7 shown in FIG. 1. A bubble level 31 is fixed in an opening in back panel 12 includes a transparent member 32 defining a bubble chamber for receiving a suitable liquid and for defining a bubble.

This permits the back panel 12 to be leveled when the test stand is used in a cross table or lateral position for supporting test objects.

The upper support panel 14 consists of a rectangular metal plate having an octagonal opening 34 surrounded by an octagonal support surface 35 formed below the upper surface of the panel 14. Panel 14 pivotally connected to the upper edge of back panel 12 by means of a pair of hinge assemblies 36, one of which is positioned adjacent each of its opposite sides. Each hinge assembly 36 includes a first hinge member 37 fixed to a hinge block 38 secured to the forward surface of back panel 12 adjacent its upper edge and a second hinge member 40 secured to the under side of panel 14 and pivotally coupled to the member 38 by a hinge pin 42. A support block 46 is fixed to the under surface of panel 14 at each lateral side and forwardly of its center line. One end of each of the upper support arms 18 is pivotally connected to one of the support blocks 46 by means of a set screw 48. As indicated above, the other end of each support arm is releasably secured to the support blocks 24 on panel 12 by thumb screws 26.

The lower support panel 16 also comprises a rectangular plate having an octagonal opening 50 surrounded by a support surface 52. An elongate hinge assembly 54 pivotally connects the lower panel 16 to the lower edge of the back panel 12. The hinge assembly 54 includes a first member 56 attached to a bar 58 fixed adjacent to lower edge of back panel 12 and a second member 60 fixed to the upper surface of bottom panel 16 adjacent its rear edge. Members 56 and 60 are pivotally connected by means of a hinge pin 62. A support block 64 is fixed to each of the lateral sides of panel 16 for pivotally receiving one end of each of the lower support arms 20 by means of a set screw 66. The other end of each of the lower arms 20 are releasably connected to the blocks 26 on base plate 22 by thumb screws 28.

It is necessary that the upper and lower panels 14 and 16 be properly oriented relative to the X-ray tube assembly. Normally, this means that each of the panels be level in a horizontal plane. Toward this end, a leveling assembly is coupled to the lower panel 16. In the illustrated embodiments the levelling assembly includes a plurality of leveling screws 68, two of which, 68a and 68b are respectively positioned at the rear corners of bottom panel 16 and a third leveling screw 68c is positioned at the center line and adjacent the forward edge of panel 16. Each leveling screw is received in a threaded opening 69 which extends through the bottom panel 16 and each has a thumb wheel 70 at its upper end. The lower end of each thumb screw 68a, 68b, and 68c extends through its respective opening 69 for engaging a support surface. The levelling assembly also includes a bubble level 71 mounted in the upper panel 14. The bubble level 71 is similar to the bubble level 31 and includes a bubble chamber 72 extending upwardly through an opening in plate 14. While a specific levelling assembly has been illustrated, those skilled in the art will appreciate that any well known leveller capable of adjustably leveling the test stand 10 may be employed.

The lower panel 16 also includes three positioning blocks 74a, 74b, and 74c. Each of the positioning blocks 74a, 74b and 74c comprises a flat, generally rectangular member having a forwardly projecting bumper, 76a, 76b, and 76c, respectively. Block 74a is positioned adjacent the rear edge of the lower plate 49 and along its center line 77 and has an elongate slot 78a extending toward the center of opening 50. A thumb screw 80a extends through slot 78a and is received in a threaded opening formed in the lower panel 16. This permits the positioning block 74a to be moved laterally and pivoted relative to the adjacent edge 50a of the opening 50. A thumb wheel 82a is disposed in the upper end of thumb screw 80a to facilitate fixing the positioning block 74a in its adjusted position.

The positioning blocks 74b and 74c are disposed adjacent the sides 50b and 50c, respectively of the octagonal opening 50 and which are the sides adjacent to the side opposite the positioning block 74a. Each of the positioning blocks 76b and 76c has a pair of slots 84 formed therein and parallel to each other and generally perpendicular to the sides 50b or 50c of opening 50. Set screws 86 extend through slots 84 and are threadably received in openings formed in the plate 49. This permits the positioning blocks 74b and 74c to be moved laterally relative to the adjacent sides 50b or 50c of opening 50. While three positioning blocks are shown in the preferred embodiment, any number which permits two dimensional adjustment of the test objects may be employed.

The first step in the testing procedure is to set up the imaging system. If the system has cinematic programs for various size patients, the program typically used for a patient in a given facility normal size patient is selected after the system has been energized. For the X-ray system of the example, the program selected for a typical patient is a large focal spot, 30 frames per second, 0.008 second pulse width, and a 10 second cine run time. Also, if the systems allows, the fluoroscopy is set to 60 kilovolts and the cine (digital) is set to 70 kilovolts (large focal spot). Next, the rotating gantry is set to zero degrees skew and zero degrees rotation. The patient table top is positioned 20.00 inches above the x-ray tube focal spot. The ion chamber probe cable is connected to the radical decimeter (X-ray monitor). The dosimeter is then turned on and set to rate mode for warm-up purposes.

After the imaging system is set up, the test stand 10 is set up and aligned. When the test stand 10 has been folded for storage, the upper and lower panels 14 and 16 are folded out and the support arms 18 and 20 are attached. The test stand 10 is then placed on the patient table 4 and positioned under the image intensifier 2.

Figure 5:
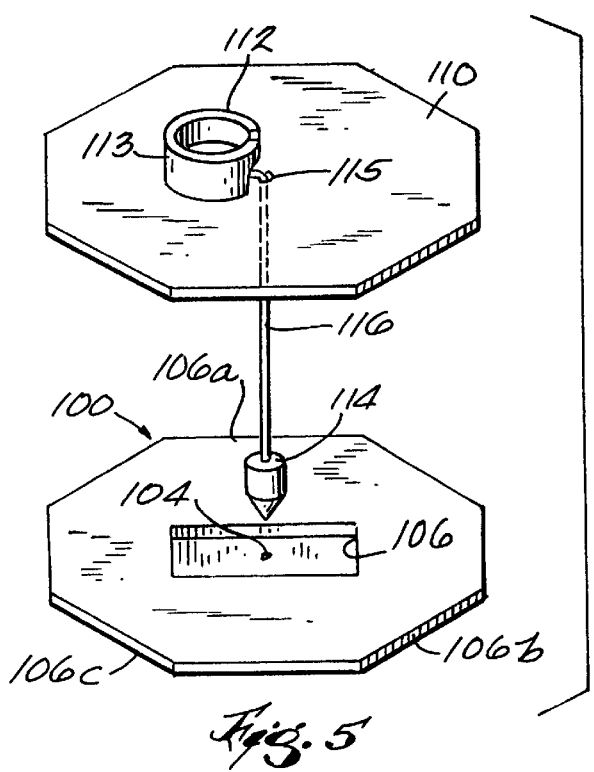
FIG. 5 illustrates how the test stand shown in FIGS. 2–4 is leveled.
Figure 5:
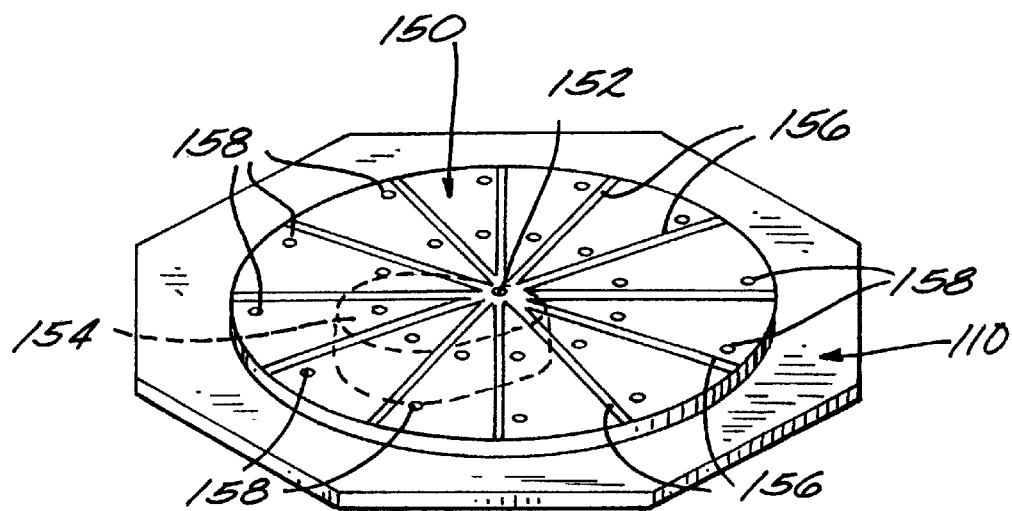

Next, the test stand 10 is leveled. First, an alignment plate 100 shown in FIG. 5 is positioned on the lower support surface 52 of the lower panel 16. The alignment plate 100 has an octagonal outer periphery and a dot 104 in its center surrounded by a rectangle 106. Edges 106a, 106b and 106c of the alignment plate 100 are abutted by the bumpers 76a, 76b and 76c, respectively. A support plate 110, as shown in FIG. 5, is positioned on the support surface 35 of the upper panel 14. The support plate 112 also has an octagonal outer periphery which mates with the periphery of the support surface 35 and includes a support collar 113 fixed to its upper surface and offset to one side of a central opening 115. A plumb bob 114 is attached by a chord 116 to an anchor receivable in support 113. The chord 116 extends through opening 115 to support the plumb bob 114 above the alignment plate 100. The test stand 10 is then leveled using the leveling screws 70b and 70c, 68a, 68b and 68c and the bubble level 67. The positioning blocks 74a, 74b and 74c are also manipulated so that the dot 104 on the positioning plate 100 is below the tip of the plumb bob 114. The alignment plate 100 and the plumb bob support plate 110 are removed from the stand 10.

An alignment field of view top plate 120 as shown in FIG. 6 is then positioned on the support surface 34 with its octagonal outer periphery 122 abutting the outer edges of the support surface 35. A radiation test shield not related to the stand is positioned in the front of the stand 10. The image intensifier of the X-ray system is set to magnitude two field of view (Mag 2FOV). The field of view plate 120 has field of view scales 123 extending in 90 degree increments around the center 124. The broken concentric circles indicate the three fields of view. With the X-ray system set at fluoroscopy, the patient table is manipulated until the center 124 of field of view plate 120 is centered to the X-ray beam. The image intensifier 2 is then set to normal non-magnified field of view and the image intensifier is slowly lowered to the top of the test stand to verify that the input surface of the intensifier is positioned parallel to the top surface of the test stand 10. If not, the image intensifier is raised from the test stand and the rotation/skew image gantry is adjusted until the input surface of the intensifier 2 is parallel to the top surface of the stand.

The openings 34 and 50 are both octagonal in the illustrated embodiment and the alignment plate 100 and the support plate 110 have octagonal outer peripheries. In addition, the support surface 35 and the support surface 52 and positioning blocks 68a, 68b and 68c define receivers for receiving the octagonal plates 100 and 110 as well as the complementary shaped octagonal phantoms and attenuators used in the testing procedure. This insures that the various plates are held in proper orientations relative to the stand 10. While octagonal shapes have been found effective for this purpose, any suitable non-circular shape which would fix the orientation of the various plates and test members may also be employed.

With the test stand level 10 and the positioning blocks 74a, 74b and 74c adjusted to center the test objects, the test stand 10 is now ready for testing an X-ray system. The tests are similar to those now performed in the prior art. These tests involve the use of various plates, attenuators, and phantoms for the purpose of testing the performance of the X-ray equipment. The test stand 10, according to the invention, facilitates the performance of these tests, and ensures accuracy and uniformity of the test results. Such tests which are commonly performed on X-ray apparatus of the type illustrated in FIG. 1 include, for example:

1. Collimator congruence/accuracy;
2. Typical fluoroscopy exposure rate;
3. Maximum permissible table top exposure rates;
4. Patient table pad absorption factor;
5. Low contrast video resolution;
6. Image intensifier field of view sizes accuracy;
7. Cine image on-frame optical density;
8. Monitor brightness/contrast;
9. Fluoroscopy/digital/cine image spacial resolution;
10. Intensifier percentage contrast;
11. Fluoroscopy/digital/cine image contrast resolution;
12. Pre-grid flurosocopy/digital/cine exposure rate; and
13. Half value layer.

For purposes of illustrating how the stand 10 according to the invention is employed, a few of these tests will be described for purposes of illustration. It will be appreciated by those skilled in the art that the list of tests discussed is not exhaustive and that additional tests may also be performed using the test stand according to the invention.

Figure 8:
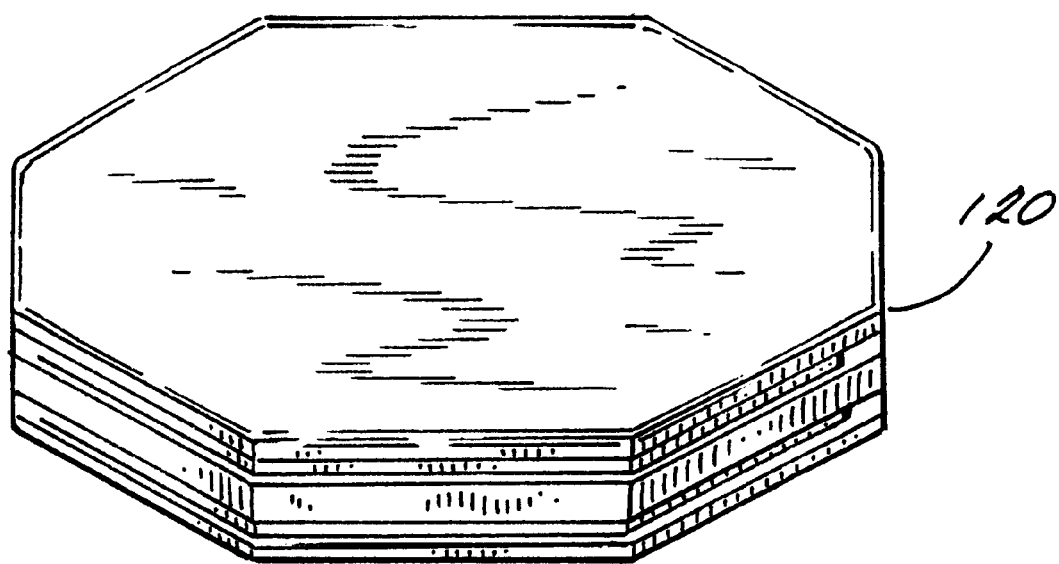

One test commonly performed is to determine the typical fluoroscopy exposure rate. First, a stack of PMMA attenuator plates 120, such as that shown in FIG. 8, are positioned above the opening 50 in the lower panel 16 by means of 2"×2" spacer blocks, or equivalents, which are placed on the support surface 52. The attenuator plates 120 are flat octagonal plates about the same size as the opening 34 in the upper panel 14, about one inch thick and formed of lucite. The attenuator plates 120 absorb about the same amount of radiation as a typical patient. The number of plates used is determined by their absorption characteristics. When one inch plates are used, about eight are equivalent to a typical individual. The dosimeter probe 6 is positioned in the opening 50 and between the 2"×2" lucite spacer blocks, or equivalents, and under the stack of lucite attenuator plates 120. Using fluoroscopy and collimation, the ionization chamber is positioned at the center of the field of view. The collimator is then opened to its widest position and the intensifier is adjusted to the normal, non-magnified field of view. Using fluoroscopy, the milliamp and kilovolt readings are recorded along with exposure values. These values represent average patient exposure values.

Another typical test is the low contrast video resolution. This test is performed using the rotating disk 150 mounted on the output shaft 152 of a motor 154 as shown in FIG. 7. The disk 150 is formed of a material such as PMMA and there are a plurality of different diameter stainless steel wires 156 embedded in the disk 150 and radiating outward in a spokelike fashion from the shaft 152. There are also a plurality of lead spheres 158 embedded in the disk 150 and arranged in 2 circular arrays around the shaft 152. The disk 150 and motor 154 are supported on the test stand by means of the support plate 110 as shown in FIG. 7. In particular, the support plate 110 is positioned on the upper panel 14 with the support collar 111 facing upwardly. The motor 150 is enclosed in the collar 111 so that shaft 152 is oriented upwardly. To simulate a "large" patient, eight one inch thick, octagonal PMMA plates and four one-half inch plates are positioned atop the lower panel 16. The intensifier 2 is then lowered to a position approximately one-half inch above the rotatable disc 150. Using fluoroscopy, the plate 150 is imaged in the first magnified FOV, while stationary and the milliamp and kilovolt exposure values and the number of wires seen while observing the monitor 5 are recorded. The diameter of the stainless steel wires 156 that are seen determines the focus. The motor 154 is then energized which rotates the disk at 30 rpm. Using fluoroscopy, the moving rotatable disk is imaged and the milliamp and kilovolt exposure values in the number of stainless steel wires seen are again recorded. In addition, if the imaging system has a last image hold capacity, the number of lead spheres images observed are also recorded. To simulate a "medium" patient, the four one-half inch blocks are removed and the process repeated.

Any other well known test can be performed using the test stand 10 but these will not be described for the sake of brevity. It will be understood that various phantoms, attenuators and other plates are positioned in the desired orientation by the upper and lower panels. The test stand 10 can also be used with the base 22 horizontal and the upper and lower panels 14 and 16 positioned vertically. When in this position, the bubble level 31 is used to level the stand.

I claim:

1. A stand for use in testing the performance of an X-ray system constructed and arranged to project an X-ray beam along a defined path, said stand including a first support for positioning a first test object at a first location relative to the path, a second support for positioning a second test object at a second position relative to the path and spaced from said first position, a receiver on at least one of the supports for receiving a test object, and a frame, each of said supports including a receiver and being mounted on the frame in a vertically spaced apart relation, one of said receivers being adjustable horizontally.

2. A stand for use in testing the performance of an X-ray system constructed and arranged to project an X-ray beam along a defined path, said stand including a first support for positioning a first test object at a first location relative to the path, a second support for positioning a second test object at a second position relative to the path and spaced from said first position, a receiver on at least one of the supports for receiving a test object, and a generally vertically extending base, each of said supports being pivotally mounted in spaced apart relation on said base, and holding members for holding each of said supports in a horizontal orientation, said holding members being releasable to permit said supports to be pivoted toward the base for storage.

3. A stand for use in testing the performance of an X-ray system constructed and arranged to project an X-ray beam along a defined path, said stand including a first support for positioning a first test object at a first location relative to the path, a second support for positioning a second test object at a second position relative to the path and spaced from said first position, and a receiver on at least one of the supports for receiving a test object, wherein the receiver has a pre-determined shape for receiving test objects having a complimentary shape and for fixing test objects in a predetermined orientation relative to the path, and wherein the receiver is adjustable in a direction perpendicular to the path so that the test objects on one support can be aligned vertically relative to the path and the test object on the other support.

4. The stand set forth in claim 3 wherein said predetermined shape is non-circular for receiving a correspondingly shaped test object and for holding the test object in a predetermined orientation relative to the path.

5. The stand set forth in claim 4 wherein one of the receivers is defined by a plurality of positioners mounted on one of the supports and being laterally adjustable relative to the path.

6. The stand set forth in claim 5 wherein the path is generally vertical, the first and second supports being spaced apart vertically, and a leveller mounted on the frame for leveling the first and second supports relative to the horizontal.

7. The stand set for in claim 6 wherein said stand includes a generally vertically extending base, each of said supports being pivotally mounted in spaced apart relation on said base, and holding members for holding each of said supports in a horizontal orientation, said holding members being releasable to permit these supports to be pivoted toward the base for storage.

8. A stand for use in testing the performance of an X-ray system constructed and arranged to project an X-ray beam along a generally vertical path, said standing including a generally vertically extending base, a first support mounted on the base for positioning test objects at a first position relative to said path, a second support mounted on the base for positioning test object at a second position relative to said path and spaced vertically from said first position, a receiver on each of said supports for supporting test objects in a vertically spaced relation along said path, an opening in each support and along the path so that an X-ray beam can pass through the supports to impart test objects on the supports, and a leveler for leveling the first and second supports relative to the horizontal, at least one of said receivers being adjustable horizontally.

9. The stand set forth in claim 8 wherein each of said supports is pivotally mounted in spaced apart relation on said frame, and holding members for holding each of said supports in a horizontal orientation, said holding members being releasable to permit the supports to be pivoted toward the frame for storage.

10. The stand set forth in claim 9 wherein each receiver has a pre-determined shape for receiving test objects having a complimentary shape and for fixing test objects in a predetermined orientation relative to the path.

11. The stand set forth in claim 10 wherein at least one of said receivers is adjustable in a direction perpendicular to the path so that the test objects on one support can be aligned vertically relative to the path and the test object on the other support.

12. The stand set forth in claim 11 wherein said predetermined shape is non-circular for receiving a correspondingly shaped test object and for holding the test object in a predetermined orientation relative to the path.

13. The stand set forth in claim 12 wherein one of the receivers is defined by a plurality of positioners mounted on one of the supports and being laterally adjustable relative to the path.

* * * * *